United States Patent [19]

Simons et al.

[11] 4,026,671
[45] May 31, 1977

[54] TEST APPARATUS CIRCUIT

[75] Inventors: Sanford L. Simons, Morrison; Frederick M. McNeill, Denver, both of Colo.

[73] Assignee: Sanford L. Simons, Morrison, Colo.

[22] Filed: Aug. 2, 1976

[21] Appl. No.: 711,038

[52] U.S. Cl. .............................. 23/259; 23/253 R; 73/64.1; 73/59

[51] Int. Cl.² ................. G01N 33/16; G01N 11/16

[58] Field of Search ......... 23/253 R, 230 R, 230 B, 23/259; 324/58.5 R, 65 R, 71 R; 73/64.1, 59

[56] References Cited

UNITED STATES PATENTS

| 3,535,084 | 10/1970 | Izawa et al. | 23/253 R |
| 3,741,002 | 6/1973 | Simons | 73/64.1 |
| 3,961,898 | 6/1976 | Neeley | 23/253 R |

Primary Examiner—R.E. Serwin
Attorney, Agent, or Firm—C. B. Messenger

[57] ABSTRACT

A circuit and apparatus combination for maintaining a balanced or regulated operational condition in test apparatus that includes mechanical drive and sensor elements as the sensor is exposed to the changing conditions experienced in a test sample or a sampled environment. The circuit automatically drives mechanical elements of the system at a resonant frequency or at other prescribed conditions with voltage changes at an output section of the circuit being indicative of changes in the sample tested or in the sensors environment. Drive elements of the circuit are powered by a drive voltage to cause movement of the sensor and the changing power thus used is evaluated and cancelled out, while a separate input or response voltage that is derived from the resulting movement of the same drive elements is introduced to an Operational Transconductance Amplifier together with an input control current likewise derived from such response voltage. The output current therefrom, which is a product of the separate input voltage times the input control current times a constant related to the transconductance amplifier, provides the changing drive voltage that is necessary to maintain the mechanical elements and sensor at their resonant or otherwise regulated and desired condition as the sensor environment changes. The changing drive voltage as the sensor is exposed to changing conditions provides a readout at an output section of the circuit that is indicative of changes in the sample or the sensor environment.

12 Claims, 3 Drawing Figures

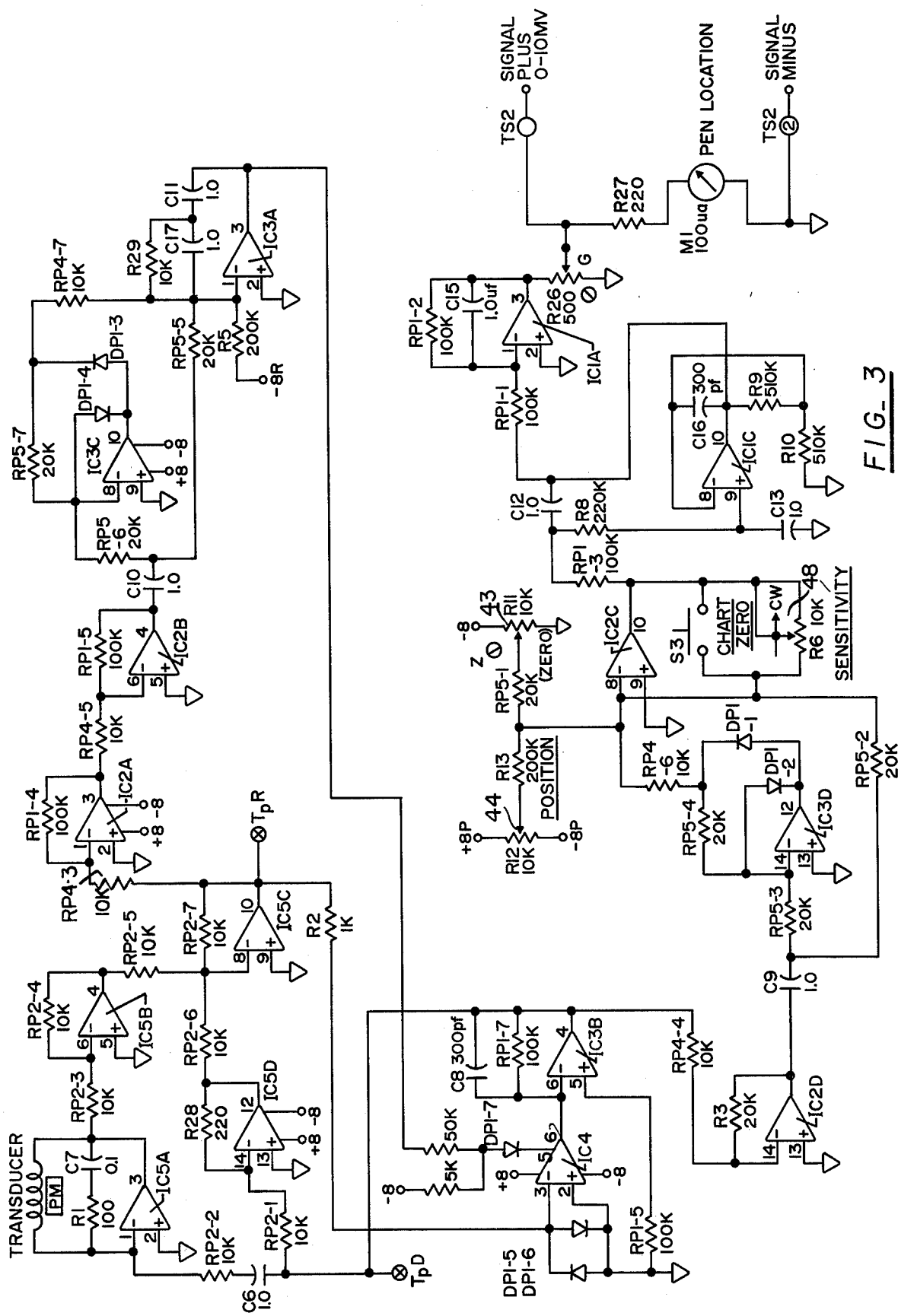
FIG_3

TEST APPARATUS CIRCUIT

BACKGROUND OF THE INVENTION

In order to provide output readings that will be indicative of certain characteristics of a fluid, earlier inventors have used probes that are disposed in contact with the fluid and that may be oscillated torsionally or reciprocally with respect thereto in order to determine the drag or other force that is exerted on the probe by the fluid. In most such apparatus power is utilized to oscillate the probe, and measurements of increasing or decreasing power requirements are used to determine the specific characteristics of the fluid then being tested. A primary usage of such type instrumentation is to determine the viscosity of a fluid either by testing samples thereof or by making near continuous readings of fluid moving past a probe sensor in a flow conduit. If a base power requirements value is established when the probe is disposed in a free air enviroment or in a liquid of known standard viscosity, an output reading showing a changed power requirement for maintaining the desired oscillating pattern for the probe can be indicative of the viscosity of other fluids being tested. The output readings of such instrumentation can be used to show changes in the shear modulus, viscosity, polymerization, flocculation, or coagulation properties of the fluid. In industrial applications such test apparatus may be used to control the intermixture of separate fluids in order to maintain a desired reading or to control polymerization processes in order to obtain a proper product.

SUMMARY OF THE INVENTION

The apparatus and circuits disclosed herein are adaptable for use in substitution for such earlier viscosity type devices, but the operation and function of the present system is herein described in connection with apparatus and components that are similiar to those shown is a previous U.S. Pat. No. 3,741,002 granted June 26, 1973, to one of the present inventors. FIGS. 1 and 2 of such prior patent are duplicated herein in order to provide additional background for explanation of the characteristics and advantages of the present circuit component development. As in the previous disclosure, the present apparatus and circuit is beneficially used to provide readout data that will be indicative of changing characteristics of body fluids. The indicated changes may be used in connection with physiological studies of the fluids or to regulate the treatment or combination of such fluids in connection with scientific and medical procedures. An important use for the present circuit development is in the field of medicine to facilitate studies of biological fluids and to determine the coagulation rates of fluids. The test results may then be indicative of deficiencies in general health, digestion or blood circulation and coagulation rates.

One specific and beneficial use of the invention has been established in connection with studies of blood and blood components. In the field of medicine the use of modern drugs and medicants that thin or thicken the blood have been hampered by the absence of methods and means for determining the already existing consistency of the blood and for further determining the prospective consistency after the administration of specific drugs. The invention provides a means and method for determining the coagulation charcteristics of whole blood samples or for samples of blood components. With the establishment of the initial and developing coagulation characteristics, the medical practitioner will be able to more efficiently determine a course for additional treatment and drug administration.

Since the coagulation characteristics of blood are dependent upon many different factors and undoubtedly on the individual combination of components in any particular sample, previous measurements and counts of blood components and of viscosities have not provided reliable information on coagulation characteristics of such samples. In a preferred embodiment instantaneous readings are indicative of the total energy transmitted to a fluid sample and the proportionate energy transmitted by or absorbed by such fluid sample with progressive readings coordinated over a period of time being used to indicate progressing changes in such readings and in the sample.

BRIEF DESCRIPTION OF THE DRAWINGS

FIG. 3 is a schematic diagram showing the circuity of a preferred embodiment.

DESCRIPTION OF THE PREFFERED EMBODIMENTS

Figure 1:
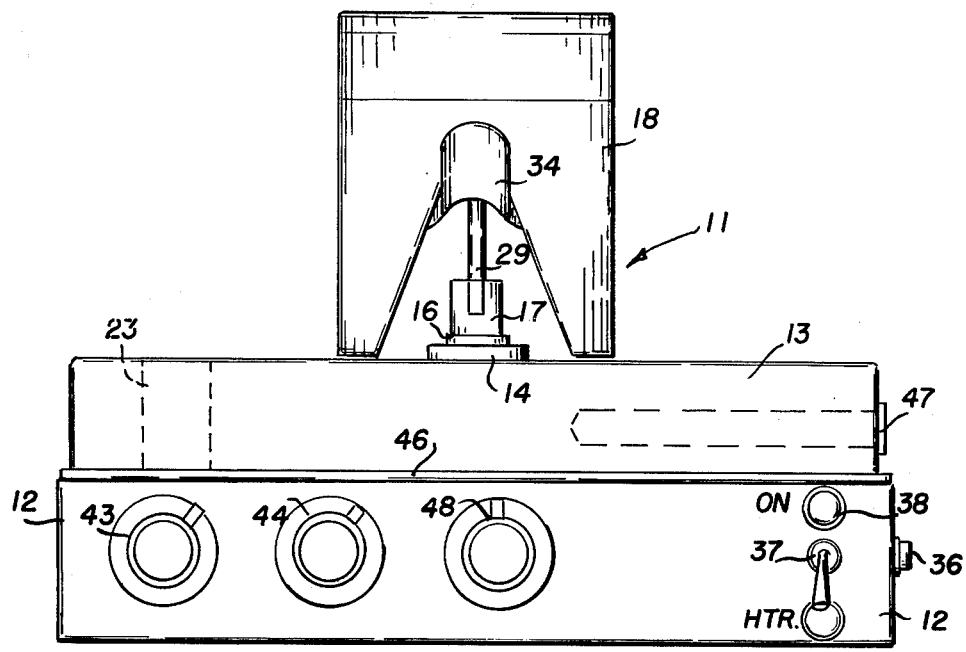
FIG. 1 is a front elevation of a preferred embodiment of the invention.
Figure 2:
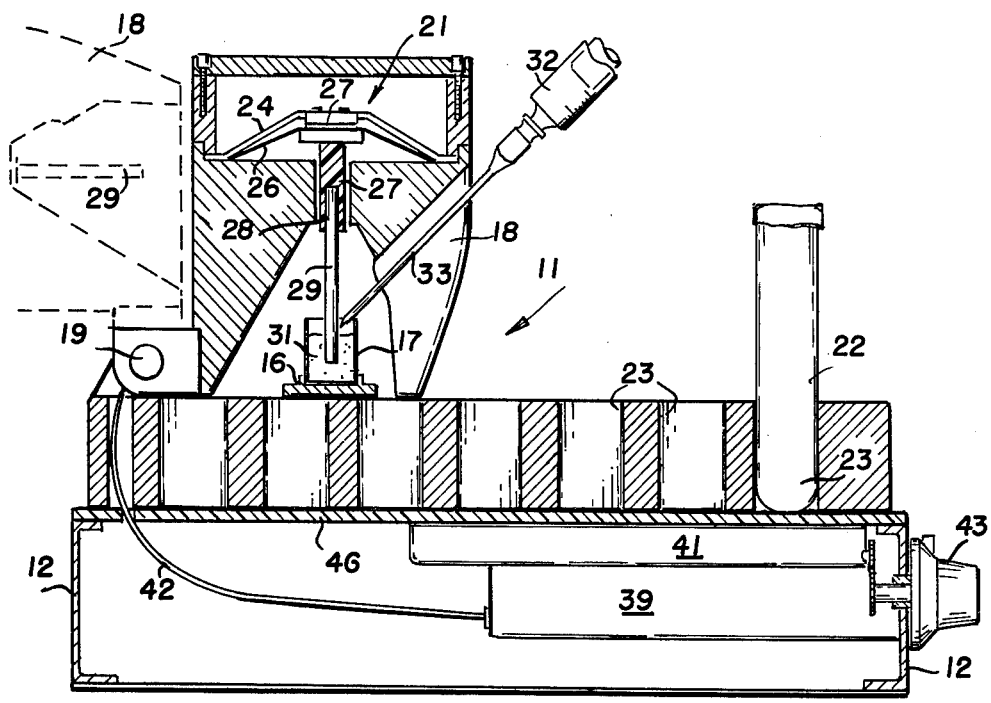
FIG. 2 is a side elevation in partial section showing additional features of such apparatus embodiment.

A preferred apparatus embodiment of the invention is shown in FIGS. 1–3. FIGS. 1 and 2 show a suitable hardware type configuration, while FIG. 3 presents a circuit diagram for the components embodied within such configuration. In FIGS. 1 and 2 the test apparatus 11 includes a base 12 of generally hollow construction upholding a heat sink-support block 13. A cup receptacle 14 is disposed centrally and rearwardly on said support 13. A ring 16 on receptacle 14 snugly receives a specimen cup 17 which may be of glass or plastic or other material so long as the interior surface is smooth and of a non-reacting substance for the particular sample. Plastic cups of the size illustrated are quite economical even when provided in sterile condition, and they, accordingly, may be used on a disposable basis.

A suitable probe or sensor driving device 21 is disposed within a pivotally mounted cover 18 that is secured to the support 13 by a hinge pin 19. The support block 13 and cover 18 are each of substantial mass so that vibrational energy imparted by the driving device 21 will not be disruptive of other laboratory procedures and will not even distrub additional blood samples that may be retained in test tubes 22 positioned in other receptacles 23 provided in support block 13.

The driving device 21 for this preferred embodiment of the invention is essentially similar to speakers used in radio work. The driving device, accordingly, has a frame 24, a cone 26 and a probe carrier 27. When the driving device (which is connected in an electronic circuit) is powered, cone 26, probe carrier 27 and a driving coil identified in FIG. 3 as the Transducer will be vibrated with respect to a permanent magnet (PM) coil on frame 24. The lower portion of probe carrier 27 is formed of resilient material, and it provides a counter bore 28 adapted to receive an end of an exciter rod or probe 29. Exciter rod-probes 29 are of a fixed length, and accordingly, when they are fully introduced into counter bore 28, they will extend a prescribed distance outwardly or downwardly therefrom so that the free end thereof will be engaged within sample cups 17 disposed in receptacle 14. With a 0.4 cc sample 31 in the cup, the free end of a probe 29 will be immersed in the sample. When the driving device 21 is powered, the essentially non-elastic exciter rod-probe 29 will be moved longitudinally in an oscillating mode to mechanically agitate the sample 31 in the cup 17.

Before initiation of vibration a quantity of recalcifier is added by a hypodermic syringe 32. A needle 33 of syringe 32 can be extended into a forward opening 34 in cover 18 so that the recalcifier can be directly applied into sample cup 17. If a one-half molar solution of calcium chloride is used as a recalcifier, it will be added in the proportion of one part $CACL_2$ to eleven parts of sample. With the recalcifier added and with a recorder or meter connected to an output jack 36 (see Signal Plus and Minus on FIG. 3), toggle switch 37 is moved to the "on" position. Indicator 38 will then light up, and probe 29 will be vibrated by the driving device 21.

For testing coagulation properties of blood samples, the driving device 21 is powered to move the Transducer and its associated probe 29 at a low frequency of 50 to 300 Hz and with low amplitude. Power as required is delivered by cable 42 past hinge pin 19 and to the driving device 21. With a meter or recorder operating and the probe in vertical position but exposed only in free air, the Zero control knob 43 may be adjusted to balance the instrument circuits. Subsequently, and with the probe in contact with a sample, position control knob 44 can be adjusted to bring the readout indication to a desired initial scale position. The sensitivity knob 48 can also be adjusted to accommodate the instrument for tests of various fluids. After completion of such initial adjustments, readings may be observed on a meter connected to signal jacks 36. If a strip recorder is used, a signal trace will be made automatically on a real time basis to indicate changes in the dampening or attenuation effects exerted by the sample on the movements patterns of the exciter rod-probe as the test is continued. Usually a total test cycle for blood sample fluids takes less than a minute to derive readings that will provide desired information relating to the characteristics of the blood sample.

Additional refinements are beneficially incorporated in this preferred embodiment of the test apparatus. Since many samples can be tested by the apparatus in a relatively short time, it is desirable that receptacles 23 be provided to hold a plurality of sample tubes 22 in convenient position alongside cover 18. Desirably the receptacle sockets 23 closely engage the sample tubes 22, and accordingly, samples may be extracted from any of the tubes 22 by use of a separate syringe. The extracted sample can be deposited directly through the opening 34 into a new sample cup 17, or the cover 18 may itself be moved to an out of way position, as shown in dotted line representation in FIG. 2, to facilitate insertion of a new sample.

In order to maintain the test samples at a regulated temperature, it is desirable that the heat sink or support block 13 be maintained at a fixed temperature. Features of a preferred heating system which utilizes the heat of power transistors is shown in an application by the same inventors filed Apr. 5, 1976, bearing Ser. No. 673,765. Such application further shows a power supply that may be used in connection with the circuit of FIG. 3 herein. For present testing operations a temperature of 37° C. has been used. A heat sensor 47 may be used.

For apparatus that is to be used for tesing blood or plasma samples, a fixed frequency can be entirely satisfactory, and for the circuit of FIG. 3 an oscillating frequency of 270 Hz is used. Satisfactory results have also been received with varous types of probes 29. These rods may be of solid glass or of various plastics. For fluids in which an end effect might be noted where a reciprocally moving solid rod is used, a hollow rod or rods of other special configuration could be used. For the maintenance of sterile conditions, it is desirable that the rods be of relatively cheap construction so that they likewise may be thrown away after the testing of each separate sample. All rod materials used in this device may be considered inelastic with respect to the power applied and its manner of application.

A representative circuit for use with the described apparatus is shown in FIG. 3. In the circuit presented in this Figure, there is a voltage that appears at Test point D (TpD) which causes a current to flow through RP2-2 into summing juntion 1 of IC5A. The same level of current flows through RP2-2. This AC current is actually introduced at the summing junctions 14 and 1 of IC5D, respectively. A coil in the feedback circuits of IC5D and IC5A, which is labeled Transducer, is actually formed of wire wound in a circular bobbin fashion. It has a resistance of about 220 ohms. The feedback resistor R28 of IC5D is also set up to have a DC resistance of about 220 ohms. The Transducer is actually free to move, but if it were held stationary, the AC voltage output of IC5A would be the same voltage as that at the output from IC5D. The output of IC5A, however, is fed into IC5B, and this integrated circuit inverts or shifts the phase of the voltage signal by 180°. The output of IC5B at pin 4 is a voltage which feeds current to RP2-5, while the output of IC5D at pin 12 is the voltage which feeds current to RP2-6. These two currents are summed at the summing junction 8 of IC5C, and if everything is balanced out, the currents cancel each other out. Accordingly, the output voltage at the output point 10 of IC5C, which corresponds to Test point R (TpR), will be zero.

The transducer, however, is actually free to move, and because it is a coiled wire located in the field of a permanent magnet (P.M.) and since it further has a current that is forced through it (which is exactly the same current that the voltage on test point D or the drive voltage pumps or forces through RP2-2), it is forced to move. When a coil moves through a magnetic field, a voltage is induced across it; and in this instance, the voltage that is induced across the coil of the Transducer due to its movement will appear at the output of IC5A to be subsequently inverted by IC5B. The resultant changed current component passing RP2-5 is summed with the current passing RP2-6 at the summing junction of IC5C. The output of IC5C at Test point R is then a voltage which is a function of the motion of the Transducer, since all other voltages introduced at IC5C are cancelled out.

The voltage at Test point R is itself delivered to two different circuits. A first circuit includes amplifier IC4, which is of special capability, since its output current at pin 6 changes as the voltage level between pins 2 and 3 is changed and as the current input at pin 5 is changed. An analog multiplier could be used to provide the desired result at this point, but a simplified and satisfactory circuit and result is obtained through use of an operational transconductance amplifier wherein the current output is a product of the voltage differential at pins 2 and 3 times the current introduced at pin 5 times a constant that is a characteristic of the device itself. When the apparatus is used, the voltage appearing at Test point R is on the order of 10 millivolts, RMS, and this voltage differential is within linear and safe operational limits for transconductance amplifiers now available.

The current output at pin 6 of IC4 is introduced to IC3B and its feedback resistor RP1-7 to produce a voltage output at pin 4 of IC3B. This is the drive voltage at Test point D that feeds into IC5A and that will cause the Transducer to move. As previously explained, the moving Transducer produces the voltage at Test point R which is used to generate the voltage at Test point D that keeps it moving. Accordingly, the cause or drive D and the Response R are effectively and cooperatively combined by these described components and circuits. In a system operating free of friction or other interference, the Transducer would continue to move at its frequency of mechanical resonance. It will move easiest at this frequency, and even the voltages that are fed back to it are in phase so it will tend to keep oscillating at its natural mechanical resonant frequency.

For the present instrument embodiment of the invention, however, it is the movement of the Transducer that is used to agitate, disrupt, move or stir the fluid that is being tested. The Transducer coil is attached to a probe 29 that engages or is engaged by the fluid that is to be tested. This interengagement of probe and fluid causes the movement pattern of the probe (and the attached Transducer) to be changed as physical properties of the fluid are changed. If the viscosity of the fluid is increased, the increase will tend to drag down or reduce the motion of the Transducer in response to the amount of energy being fed to it from the drive voltage. In order to maintain the previous frequency and/or amplitude of Transducer motion, some additional energy input is required that will increase the voltage at Test point D. Since the required increased drive voltage input that may be necessary to maintain the movement pattern for the probe may be indicative of changing physical characteristics for the test sample fluid, additional circuits are provided that will, first, preserve the Transducer movement and, secondly, provide a readout indication of the changed power levels as the sample is subjected to the testing procedure. To obtain this desired result a second circuit is connected at Test point R. This second circuit feeds the signal at point R which is a measure of the voltages derived from movement of the Transducer into IC2A and its feedback resistors where it is amplified by 10, and subsequently to IC2B and its feedback resistors where it is further amplified by 10. Accordingly, the approximate 10 millivolt output at point R provides a one volt feed into IC3C and its associated diodes and resistors. This one volt input is passed through C10 before introduction to the precision halfway rectifier provided by IC3C and its circuits to remove any DC voltage that might have been present at IC2B, and only the AC wave form will be rectified. The AC wave form from IC2B also feeds current through RP5-5. The current through RP5-5 at any given voltage is half the current fed through RP4-7, since RP4-7 is half the value of RP5. The summing of those two currents produces a current at the summing junction 1 of IC3A of a full wave rectified AC. A DC current through R5 is also introduced at that summing junction. The summation of all those currents is integrated by C11. If the summation is different from zero, then the output of IC3A increases or decreases to make up the difference so that the current summed at the summing junction is forced to be zero. The output voltage of IC3A is used to drive a current through a 50K resistor that is in series with diode DP1-7 and in parallel with a 5K resistor in a −8 volt source. The voltage signal from IC3A provides a positive current into pin 5 for IC4 of a level such that the product of such current and the voltage at Test point R times a constant related to the transconductance amplifier IC4 will produce a current at the summing junction of IC3B as necessary to provide a voltage at the output of IC3B or at TpD, which is the drive voltage that needs to be fed back into the Transducer and its balancing op amp IC5D to keep the Transducer and its probe moving at its resonant frequency and/or at the chosen amplitude. The result is that the voltage at Test point R is forced to be constant, even though the Transducer experiences more drag as when the viscosity of the test sample increases. If drag is increased, the voltage at Test point D (TpD) will increase to maintain the constant amplitude of motion for the Transducer that will cause the voltage at Test point R (TpR) to be constant.

In order to provide an output signal that will indicate the drive forces acting on the probe, the test point drive voltage is picked off and fed into the amplifier circuits of IC2D and its associated feedback resistors for a two-to-one increase. Capacitor C9 then allows only the AC voltage from the output of IC2D to be fed into another precision halfway rectifier, inclusive of its associated op amps IC3D and IC2C. The feedback circuits of IC2C include sensitivity pot 48 of the front panel, which corresponds to R6-10K in the circuit diagram of FIG. 3. This may be adjusted by the customer to accommodate various sensitivities required by the different viscosities of samples that may be tested.

The output of IC2C at pin 10 is dependent on three separate inputs. The then rectified and pulsating AC voltage from IC3D is summed with the voltage coming from R11 through RP5-1. R11 has a variable resistance, and it is used to provide a zero setting when the Transducer probe 29 is oscillating or vibrating in free air. Variable resistance pot R11 corresponds to control 43 of FIG. 1 and is further identified by such number and the legend Zero on FIG. 3. With free air conditions for the sensor-probe 29, the voltage at IC2C should effectively be zero. After a zero setting has been obtained, the probe 29 can be rotated to its position of contact with the sample to be tested, and thereafter the variable resistance pot R12 (identified as 44 in FIG. 1 and further by the legend Position on FIG. 3) may be adjusted to bring the pen location meter to a somewhat centered or otherwise regulated position corresponding to the samples then being run. This meter, which in the present circuit is a 100 microamp meter, is used when the output singnal is to be applied to a 0 to 10 millivolt strip chart recorder. In general, the particular meter position that is established through experience can be used to assure the test operator that the signal traces recorded on a strip chart recorder will remain on scale if the test is started at the chosen pen location position of the milliamp meter.

The signal from variable resistance pot R12 passes through the resistance R13 and is connected to the input pin 8 of IC2C. The output at pin 10 of IC2C is then dependent upon the drive voltage being applied to the Transducer and the adjustment voltages passing the zero and Position potentiometers. This output signal is introduced to a 1 Hz low pass roll off type filter represented by IC1C. This filter is provided to filter out any of the frequencies that might be introduced to these signal level readout components as the result of the vibration of the Transducer. Since the Transducer in the present circuit vibrates at around 270 Hz, any disturbance due to such vibrations will be filtered out by IC1C. The output from IC1C, accordingly, is a DC voltage that is a function of the drive voltage or driving force applied to the Transducer. Since this driving force will be increased to maintain a resonant frequency for the Transducer as the drag on probe 29 is increased, as when the viscosity of the sample increases, the signal at IC1C is a function of the change of viscosity experienced by the Transducer and its probe. The output signal voltage at pin 10 of IC1C is put back through RP1-1 to IC1A. The output from this component is attenuated by the variable resistance R26 identified by the legend G for gain and resistance R27 which is disposed across the Signal output Plus and Minus terminals which correspond to the jack 36 of FIG. 1. These output terminals may be connected to a strip chart recorder to give a real time readout of the changes in the sample being tested. Where blood or blood fractions are being tested, a characteristic curve as set forth in the mentioned earlier U.S. Pat. No. 3,741,002 will be obtained.

Some additional features of the circuit shown in FIG. 3 should be mentioned. The capacitor C8 at IC3B is provided to keep this op amp from oscillating. Similarly, resistance R1 and capacitor C7 are disposed across the Transducer to prevent IC5A from oscillating due to the inductance associated with the Transducer and the active bridge coupled thereto which would include the O.T.A. IC4. The capacitor C6 is provided adjacent TpD to decouple any DC voltage that might appear at such point. The Operational Transconductance Amplifier O.T.A. used in this circuit and identified as IC4 is commercially identified as R.C.A. Model CA-3080. A top limit for linear operation of this O.T.A. is approximately 50 millivolts. Accordingly, the diodes DP1-5 and DP1-6 are used together with R2 to clamp the input into IC4. This combination will prevent damage to the O.T.A. if the Transducer is disconnected from the circuit.

In summary of this circuit and its operation, it should be noted that a driving voltage or drive force is applied to the Transducer to cause it to vibrate. The same drive voltage is applied in a separate leg of a bridge arrangement to components equivalent to those associated with the Transducer, and the output on one leg is inverted before it is recombined. With this arrangement the net output includes only a response voltage or response force signal which is derived from the fact that the Transducer coil moves in the flux field of a permanent magnet. This response force signal is held at a desired level corresponding to a desired amplitude of movement for the Transducer and its probe, and any change in the reponse signal level causes a decrease or increase with respect to the desired response signal level is then used to respectively increases or decreases the input drive voltage. Accordingly, if the probe connected to the Transducer encounters increased drag due to changes in the sample being tested, the response force will tend to decrease. Since the response force is balanced with respect to a desired output, the resulting decrease in the response force as applied to balance circuits will cause the increase in the drive voltage that is applied until the desired amplitude of vibration is again obtained. The circuit then is self-regulating and tends to maintain a regulated response force. At the same time signal components of the circuit are provided which sense the instantaneously applied driving voltage or drive force. Increases and decreases in the drive voltage then provide changes in the output signals which are indicative of changes in the viscosity of the sample being tested or at least of the drag being exerted on the probe by the sample as the characteristics of the sample are changed.

While the device is described in connection with the testing of biological fluids, the same components and the same circuit arrangement can be used for studies of the viscosities of fluids or to control intermixture of separate fluids. Polymerization studies of compounds and studies of Newtonian and non-Newtonian effects in fluids are facilitated through use of this apparatus and circuit.

We claim

1. A circuit arrangement for test apparatus used to determine properties of fluids comprising an oscillating probe disposed in contact with the fluid to be tested, a source of electric power, electro-mechanical means interconnected to said electric power source to provide a driving force component for mechanically oscillating said probe, said electro-mechanical means being inclusive of co-active conductor and magnet elements that are moved one with respect to the other by the applied driving force and with said probe moving with one of said elements, a sensor circuit connected to said conductor element for sensing a response force signal component generated therein due to relative movement of said conductor with respect to the flux field of said magnet elements, balance circuits for changing the driving force component as necessary to maintain a desired response force, and means providing a signal level readout indication of the changing levels for the driving force component applied as the desired response force is maintained.

2. The circuit arrangement of claim 1 wherein the output from said conductor is inclusive of both driving force and response force components.

3. The circuit arrangement of claim 2 wherein the driving force component that is applied to said electro-mechanical means is additionally applied to an inverting balancing circuit whereby said driving force component is cancelled and only the response force signal component is applied to said sensor circuit.

4. The circuit arrangement as set forth in claim 3 wherein said inverting balancing circuit is inclusive of a resistance related to the resistance of said conductor.

5. The circuit arrangement as set forth in claim 1 wherein the output of said sensor circuit is indicative of changes in said response force away from a desired norm.

6. The circuit arrangement as set forth in claim 5 wherein said driving force balance circuit is inclusive of multiplier components and the output of said sensor circuit is interconnected thereto.

7. The circuit arrangement as set forth in claim 5 wherein the output of said sensor circuit is a current that is indicative of changes in said response force.

8. The circuit arrangement as set forth in claim 5 wherein said driving force balance circuit is inclusive of an operational transconductance amplifier and the output of said sensor circuit is interconnected thereto.

9. The circuit arrangement as set forth in claim 1 wherein said electro-mechanical means and the conductor thereof is inclusive of a single coil for oscillating said probe and for generating said response force.

10. The circuit arrangement as set forth in claim 9 wherein said coil moves with said probe.

11. The circuit arrangement as set forth in claim 1 wherein said test apparatus is used for the observation of properties of fluids that change on a time basis, and further comprising means for maintaining said response force constant during an expected period of observation whereby the signal level readout of changes in said driving force component is indicative of the changed properties of said fluid.

12. The circuit arrangement as set forth in claim 11 wherein said test apparatus is used to determine the coagulation properties of biological fluids and wherein said probe is oscillated longitudinally in contact with said biological fluids during the period of observation.

* * * * *

UNITED STATES PATENT OFFICE
CERTIFICATE OF CORRECTION

Patent No. 4,026,671　　　　　　　Dated May 31, 1977

Inventor(s) Sanford L. Simons and Frederick H. McNeill

It is certified that error appears in the above-identified patent and that said Letters Patent are hereby corrected as shown below:

Column 4, lines 25 and 26, change to read as follows:
    IC5D and IC5A, respectively. A coil in the feedback
    circuits of IC5A, which is labeled Transducer, is actu- Column 6, line 60, change "singnal" to read "signal".

Column 7, line 63, after "level" insert -- that -- .

Column 7, line 65, change "increases or decreases" to read "increase or decrease".

Signed and Sealed this twenty-third Day of August 1977

[SEAL]

Attest:

RUTH C. MASON
Attesting Officer

C. MARSHALL DANN
Commissioner of Patents and Trademarks